(12) United States Patent
Kato et al.

(10) Patent No.: US 9,895,459 B2
(45) Date of Patent: Feb. 20, 2018

(54) ULTRAVIOLET RAY EMITTING PACKAGE HAVING RESIN ADHESIVE LAYER AND ULTRAVIOLET RAY IRRADIATING APPARATUS

(71) Applicant: Stanley Electric Co., Ltd., Tokyo (JP)

(72) Inventors: Hiroyuki Kato, Kanagawa (JP); Kazuyoshi Taniguchi, Kanagawa (JP); Junji Matsuda, Kanagawa (JP); Tsutomu Ohkubo, Tokyo (JP)

(73) Assignee: STANLEY ELECTRIC CO., LTD., Tokyo (JP)

( * ) Notice: Subject to any disclaimer, the term of this patent is extended or adjusted under 35 U.S.C. 154(b) by 0 days.

(21) Appl. No.: 15/291,375

(22) Filed: Oct. 12, 2016

(65) Prior Publication Data
US 2017/0112952 A1    Apr. 27, 2017

(30) Foreign Application Priority Data

Oct. 21, 2015  (JP) ................... 2015-206883
Feb. 15, 2016  (JP) ................... 2016-025535
Aug. 25, 2016  (JP) ................... 2016-164366

(51) Int. Cl.
| | |
|---|---|
| *G21K 5/00* | (2006.01) |
| *A61L 2/10* | (2006.01) |
| *F21V 3/02* | (2006.01) |
| *F21V 19/00* | (2006.01) |
| *F21V 11/00* | (2015.01) |
| *F21Y 115/10* | (2016.01) |

(52) U.S. Cl.
CPC .................... *A61L 2/10* (2013.01); *F21V 3/02* (2013.01); *F21V 11/00* (2013.01); *F21V 19/002* (2013.01); *F21Y 2115/10* (2016.08)

(58) Field of Classification Search
CPC .... H05G 2/003; H05G 2/008; G03F 7/70033; G03F 7/70916; B82Y 10/00
USPC ... 250/493.1, 504 R, 504 H, 453.11, 454.11, 250/455.11
See application file for complete search history.

(56) References Cited

U.S. PATENT DOCUMENTS

| | | | |
|---|---|---|---|
| 2006/0121184 A1* | 6/2006 | Minamio | .......... H01L 27/14618 427/162 |
| 2009/0256260 A1* | 10/2009 | Nakamura | ........ H01L 27/14618 257/758 |
| 2010/0252804 A1* | 10/2010 | Cheng | .................... H01J 1/304 257/10 |
| 2012/0267671 A1* | 10/2012 | Jung | .................... H01L 33/486 257/99 |

(Continued)

FOREIGN PATENT DOCUMENTS

| | | |
|---|---|---|
| JP | 2012-227511 A | 11/2012 |
| JP | 2015-18873 A | 1/2015 |

*Primary Examiner* — Nicole Ippolito
(74) *Attorney, Agent, or Firm* — Kenealy Vaidya LLP

(57) ABSTRACT

An ultraviolet ray emitting package includes: a substrate having an upper portion defining a recess; an ultraviolet ray emitting element provided within the recess of the substrate; an ultraviolet ray transmitting window member provided on the upper portion of the substrate to cover the recess of the substrate; a resin adhesive layer provided between the upper portion of the substrate and the ultraviolet ray transmitting window member; and an optical shielding layer provided between the resin adhesive layer and the ultraviolet ray transmitting window member.

16 Claims, 17 Drawing Sheets

(56) References Cited

U.S. PATENT DOCUMENTS

2015/0041767 A1\* 2/2015 Yu .................... H01L 51/524
 257/40

\* cited by examiner

| ORGANIC GROUP | BOND ENERGY (kcal/mol) | ENERGY-REDUCED WAVELENGTH (nm) |
|---|---|---|
| C≡N | 222.2 | 128.6 |
| C=O | 190.0 | 150.4 |
| C≡C | 188.8 | 151.4 |
| Si-O | 150.0 | 190.5 |
| C=C | 140.5 | 203.4 |
| H-F | 134.9 | 211.9 |
| O=O | 117.5 | 243.2 |
| C-F | 115.2 | 248.1 |
| O-H | 109.3 | 261.5 |
| H-Cl | 101.9 | 280.5 |
| C-H | 97.6 | 292.8 |
| N-H | 91.9 | 311.0 |
| C-C | 84.3 | 339.0 |
| C-Cl | 76.9 | 371.7 |
| C-O | 76.4 | 374.1 |
| C-N | 63.6 | 449.4 |
| O-O | 32.9 | 868.7 |

ULTRAVIOLET RAY EMITTING PACKAGE HAVING RESIN ADHESIVE LAYER AND ULTRAVIOLET RAY IRRADIATING APPARATUS

This application claims the priority benefit under 35 U.S.C. § 119 to Japanese Patent Application Nos. JP2015-206883, JP2016-25535 and JP2016-164366 filed on Oct. 21, 2015, Feb. 15, 2016 and Aug. 25, 2016, respectively, which disclosures are hereby incorporated in their entirety by reference.

BACKGROUND

Field

The presently disclosed subject matter relates to an ultraviolet ray emitting package having a resin adhesive layer and an ultraviolet ray irradiating apparatus using the same.

Description of the Related Art

Generally, a deep ultraviolet ray emitting package for emitting a deep-ultraviolet ray with a short wavelength of about 210 to 310 nm is used for disinfection, sterilization, purification and so on, while an ultraviolet ray emitting package for emitting an ultraviolet ray with a long wavelength of about 310 nm or more is used for exposure and so on.

In FIG. 14, which illustrates a first prior art ultraviolet ray emitting package (see: US2012/0267671A1 & JP2012-227511A), this package 100 is constructed by a substrate 101 with a recess (cavity) 101a defined by an upper portion 101b of the substrate 101, ultraviolet ray (light) emitting diode (LED) elements 102 provided within the recess 101a of the substrate 101, an ultraviolet ray transmitting window member 103 covering the recess 101a of the substrate 101, and a resin adhesive layer 104 serving as a sealing member provided between the upper portion 101b of the substrate 101 and the ultraviolet ray transmitting window member 103. For example, the resin adhesive layer 104 is made of an Ag paste, an ultraviolet (UV) adhesive, Pb-free low-temperature glass, an acryl adhesive or a ceramic adhesive (see: paragraph 0095 of US2012/0267671A1).

In FIG. 14, ultraviolet rays UL1 generated from the ultraviolet LED elements 102 pass through the ultraviolet ray transmitting window member 103 to the outside. On the other hand, ultraviolet rays UV2 generated from the ultraviolet LED elements 102 are incident to the ultraviolet ray transmitting window member 103 and are reflected within the ultraviolet ray transmitting window member 103 to reach the resin adhesive layer 104. Also, ultraviolet rays UV3 generated from the ultraviolet LED elements 102 directly reach the resin adhesive layer 104.

In the ultraviolet ray emitting package 100 of FIG. 14, the resin adhesive layer 104 is irradiated with the ultraviolet rays UV2 and UV3 from the ultraviolet LED elements 102. In this case, since the traverse face of the resin adhesive layer 104 is much larger than the lateral face thereof, the irradiation amount with the ultraviolet rays UV2 is much larger than that with the ultraviolet rays UV3. When the resin adhesive layer 104 includes organic groups, some of the organic groups would be cut by the irradiation with the ultraviolet rays UV2 and UV3, so that the resin adhesive layer 104 would be chemically-modified causing it to deteriorate. For example, organic groups N—H, C—C, ..., O—O as indicated by R1 in FIG. 15 would be cut by the irradiation with ultraviolet rays whose wavelength is 310 nm or more. If the ultraviolet rays UV2 and UV3 are deep-ultraviolet rays whose wavelength is about 210 to 310 nm, organic groups H—F, O═O, ..., O—O as indicated by R2 in FIG. 15 would be cut by the irradiation with such deep-ultraviolet rays. Therefore, when the resin adhesive layer 104 is chemically-modified so as to deteriorate, cracks and changes in color would be generated in the resin adhesive layer 104 to degrade the adhesive ability, thus degrading the reliability of the ultraviolet ray emitting package 100 of FIG. 14.

Also, as illustrated in FIG. 16A, when the ultraviolet ray emitting package 100 is arranged on an outer face of an ultraviolet ray transmitting casing 111 in which processing gas or water to be sterilized flows indicated by an arrow AR, and a reflective plate 112 opposing the ultraviolet ray emitting package 100 is provided on the outer face of the ultraviolet ray transmitting casing 111, ultraviolet rays UV generated from the ultraviolet ray emitting package 100 are reflected by the reflective plate 112, so that some of the ultraviolet rays UV would return to the ultraviolet ray emitting package 100. Additionally, as illustrated in FIGS. 16B and 16C, when an additional ultraviolet ray emitting package 100', similar to the ultraviolet ray emitting package 100, opposing the ultraviolet ray emitting package 100 is provided on an outer face of the ultraviolet ray transmitting casing 111 without the reflective plate 112 of FIG. 16A, some of ultraviolet rays UV generated from the ultraviolet ray emitting package 100 are incident to the ultraviolet ray emitting package 100', and simultaneously, some of ultraviolet rays UV' generated from the ultraviolet ray emitting package 100' are incident to the ultraviolet ray emitting package 100. Therefore, the resin adhesive layer 104 of each of the ultraviolet ray emitting packages 100 and 100' is chemically-modified by the radiation with the ultraviolet rays UV' and UV, respectively, so as to deteriorate, cracks and changes in color are generated in the resin adhesive layer 104 to degrade the adhesive ability, thus degrading the reliability of the ultraviolet ray emitting packages 100 and 100'.

Further, when the ultraviolet ray transmitting window member 103 is adhered by the resin adhesive layer 104 to the upper portion 101b of the substrate 101, the ultraviolet ray transmitting window member 103 would slide along the traverse direction due to a temporary reduction of the viscosity of the resin adhesive layer 104.

In FIG. 17, which illustrates a second prior art ultraviolet ray emitting package (see: JP2015-18873A), this package 200 includes a metal layer 201 provided on the side of the substrate 101, a metal layer 202 provided on the side of the ultraviolet ray transmitting window member 103, and an AuSn (or AgSn) eutectic bonding layer 203 provided between the metal layers 201 and 202, instead of the resin adhesive layer 104 of FIG. 14.

In the ultraviolet ray emitting package 200 of FIG. 17, ultraviolet rays UV2 generated from the ultraviolet LED elements 102 are reflected within the ultraviolet ray transmitting window member 103 to irradiate the metal layer 202, and also, the metal layer 202 is irradiated directly with the ultraviolet rays UV3. Even in this case, the AuSn eutectic bonding layer 203 would not be chemically-modified which would cause it to deteriorate. However, since the AuSn eutectic bonding layer 203 would invite a high manufacturing cost, the ultraviolet ray emitting package 200 of FIG. 17 would be high in manufacturing cost.

SUMMARY

The presently disclosed subject matter seeks to solve the above-described problems.

According to the presently disclosed subject matter, an ultraviolet ray emitting package includes: a substrate having an upper portion defining a recess; an ultraviolet ray emitting element provided within the recess of the substrate; an ultraviolet ray transmitting window member provided on the upper portion of the substrate to cover the recess of the substrate; a resin adhesive layer provided between the upper portion of the substrate and the ultraviolet ray transmitting window member; and an optical shielding layer provided between the resin adhesive layer and the ultraviolet ray transmitting window member. Thus, the ultraviolet rays reflected within the ultraviolet ray transmitting window member to irradiate the resin adhesive layer can be suppressed by the optical shielding layer.

Also, the ultraviolet ray transmitting window member includes a protrusion fitted into the recess of the substrate.

Thus, when the ultraviolet ray transmitting window member is adhered by the resin adhesive layer to the upper portion of the substrate, traverse sliding of the ultraviolet ray transmitting window member due to the temporary reduction of viscosity of the resin adhesive layer can be suppressed by the sidewall of the protrusion.

Further, an outer step or a recess is provided in the upper portion of the substrate, and the resin adhesive layer is provided in the outer step or the recess. Thus, the ultraviolet rays from the ultraviolet ray emitting element directly to the resin adhesive layer can be suppressed.

According to the presently disclosed subject matter, since the optical shielding layer is provided on the resin adhesive layer, ultraviolet rays reflected within the deep-ultraviolet ray transmitting window member can be reflected and/or absorbed by the optical shielding layer, so that the resin adhesive layer is not subjected to irradiation of ultraviolet rays. Therefore, the resin adhesive layer would not be chemically-modified which would cause it to deteriorate, so that the adhesive ability of the resin adhesive layer would not be degraded thus improving the reliability of the deep-ultraviolet ray emitting package.

BRIEF DESCRIPTION OF THE DRAWINGS

The above and other advantages and features of the presently disclosed subject matter will be more apparent from the following description of certain embodiments, as compared with the prior art, taken in conjunction with the accompanying drawings, wherein.

DETAILED DESCRIPTION OF EXEMPLARY EMBODIMENTS

Figure 1:
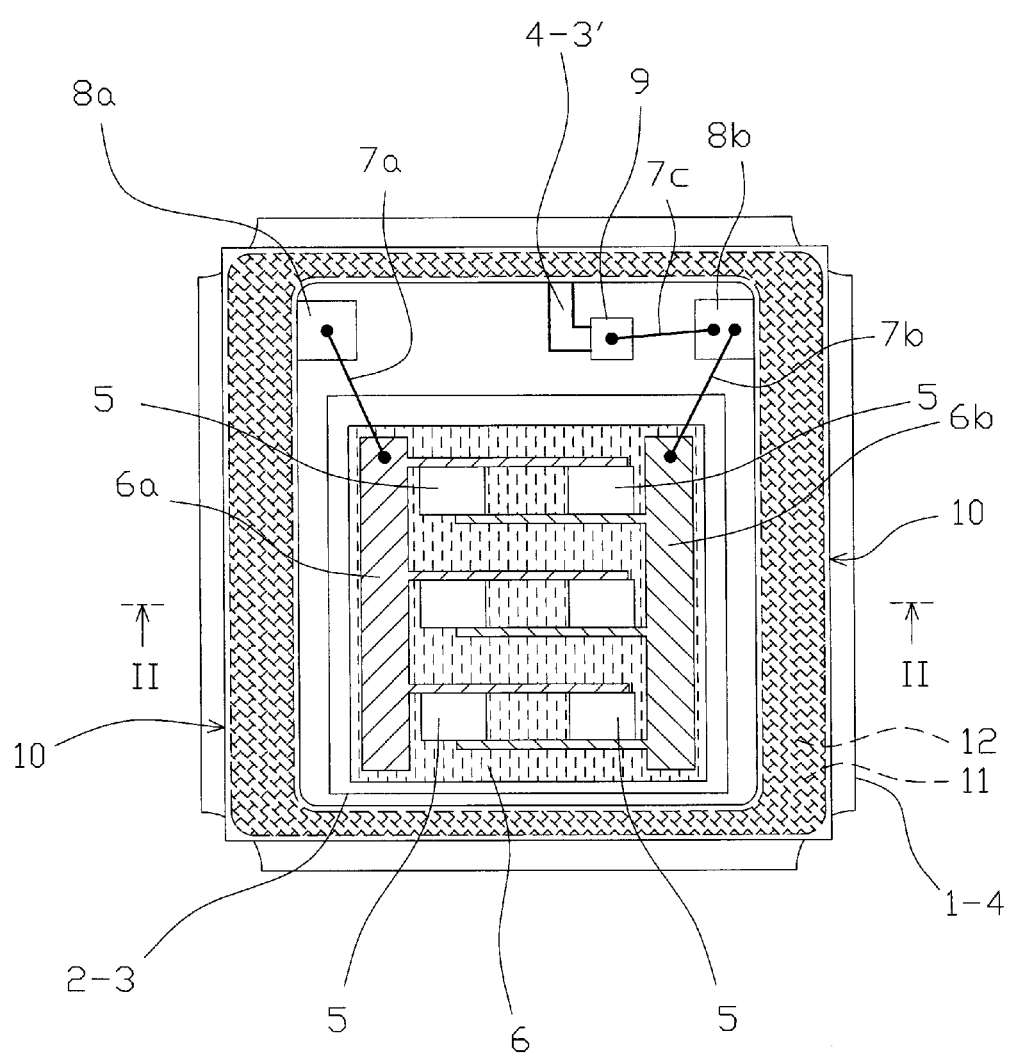
FIG. 1 is a plan diagram illustrating a first embodiment of the deep-ultraviolet ray emitting package according to the presently disclosed subject matter.
Figure 2:
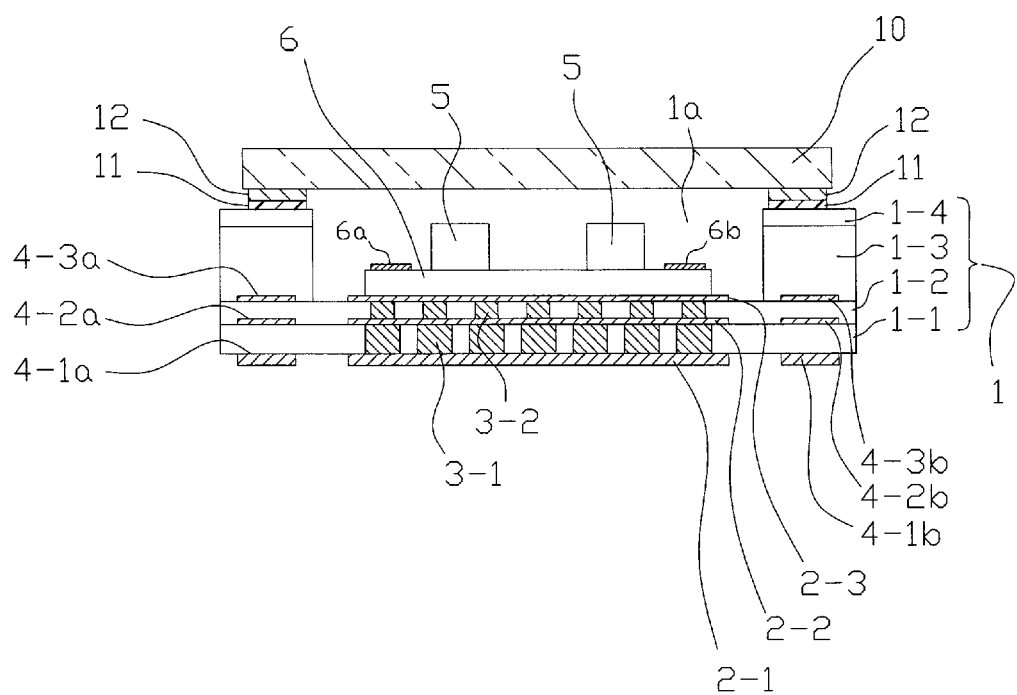
FIG. 2 is a cross-sectional view taken along the line II-II in the deep-ultraviolet ray emitting package of FIG. 1.

FIG. 1 is a plan diagram illustrating a first embodiment of the deep-ultraviolet ray emitting package according to the presently disclosed subject matter, and FIG. 2 is a cross-sectional view taken along the line II-II of FIG. 1.

In FIGS. 1 and 2, a low temperature co-fired ceramics (LTCC) substrate 1 is formed by four laminated insulating ceramics substrates 1-1, 1-2, 1-3 and 1-4. In this case, a recess 1a is defined by the substrates 1-3 and 1-4 which are frame-shaped.

At the recess 1a of the LTCC substrate 1, a heat-dissipating pad 2-1 is provided at a bottom face of the substrate 1-1, a heat-dissipating pad 2-2 is provided between the substrates 1-1 and 1-2, and a heat-dissipating pad 2-3 is provided on a top face of the substrate 1-2. The heat-dissipating pads 2-1 and 2-2 are coupled by metal via-structures 3-1, and the heat-dissipating pads 2-2 and 2-3 are coupled by metal via-structures 3-2. In this case, the diameter of the metal via-structures 3-1 is larger than the diameter of the metal via-structures 3-2, in order to enhance the heat-dissipating efficiency. For example, the diameter of the metal via-structures 3-1 is about 0.3 mm, while the diameter of the metal via-structures 3-2 is about 0.25 mm. The metal via-structures 3-1 and 3-2 are made of Ag or its alloy, and Pt, Rh, Pd or Ru can be added thereto, as long as the sintering of Ag or its alloy is not impeded.

Under the substrates 1-3 and 1-4 forming an upper portion defining the recess 1a, electrode pads 4-1a and 4-1b are provided on a bottom face of the substrate 1-1, connection pads 4-2a and 4-2b are provided between the substrates 1-1 and 1-2, and connection pads 4-3a and 4-3b are provided on a top face of the substrate 1-4. Respective ones of the electrode pads 4-1a and 4-1b and respective ones of the connection pads 4-2a and 4-2b are coupled by metal via-structures (not shown) similar to the metal via-structures 3-1. Also, respective ones of the connection pads 4-2a and 4-2b and respective ones of the connection pads 4-3a and 4-3b are coupled by metal via-structures (not shown) similar to the metal via-structures 3-2.

Six deep-ultraviolet LED elements 5, which have AlGaN-based active regions for emitting deep-ultraviolet rays with a frequency of about 210 to 310 nm, are mounted by AuSn eutectic bonding layers or bumps (not shown) on a submount 6. The number of the deep-ultraviolet LED elements 5 can be other numbers such as 1, 2, 3, 4, 5, 7, . . . . The submount 6, which is made of AlN or silicon with silicon oxide, is bonded by an AuSn eutectic layer (not shown) on the heat-dissipating pad 2-3. Therefore, heat generated from the deep-ultraviolet LED elements 5 can be effectively dissipated through the submount 6, the dissipating pad 2-3, the metal via-structures 3-2, the heat-dissipating pad 2-2, the metal via-structures 3-1 and the heat-dissipating pad 2-1 to the outside.

The deep-ultraviolet LED elements 5 are electrically connected between connection layers 6a and 6b on the submount 6. The connection layers 6a and 6b are electrically connected by wires 7a and 7b to wire bonding pads 8a and 8b, respectively, on the substrate 1-2. The wire bonding pads 8a and 8b coupled to the connection pads 4-3a and 4-3b are electrically connected through the connection pads 4-2a and 4-2b to the electrode pads 4-1a and 4-1b. Thus, the deep-ultraviolet LED elements 5 are electrically connected between the electrode pads 4-1a and 4-1b.

A Zener diode 9 is anti-parallelly connected to the deep-ultraviolet LED elements 5 in order to prevent the deep-ultraviolet LED elements 5 from being in a reverse voltage state. An electrode of the Zener diode 9 is mounted on a connection pad 4-3', similar to the connection pads 4-3a and 4-3b, on the substrate 1-2, while another electrode of the Zener diode 9 is electrically connected by a wire 7c to the wire bonding pad 8b. The connection pad 4-3' is electrically connected to an electrode pad (not shown) similar to the electrode pads 4-1a and 4-1b.

Note that the heat-dissipating pad 2-1 and the electrode pads 4-1a and 4-1b are constructed by the same layer; the heat-dissipating pad 2-2 and the connection pads 4-2a and 4-2b are constructed by the same layer; and the heat-dissipating pad 2-3, the connection pads 4-3a, 4-3b and 4-3' and the wire bonding pads 8a and 8b are constructed by the same layer.

A plate-type deep-ultraviolet ray transmitting window member 10 is provided on the substrate 1-4 of the LTCC substrate 1 to cover the recess 1a thereof. The deep-ultraviolet ray transmitting window member 10 is made of deep-ultraviolet ray transmitting material such as quartz a glass, sapphire, MgO, MgF$_2$, CaF$_2$ and synthetic fused silica.

Provided between the substrate 1-4 and the deep-ultraviolet ray transmitting window member 10 is a resin adhesive layer 11 as a sealing member. The resin adhesive layer 11 is made of acryl-based resin, epoxy-based resin, silicone-based resin, organic/inorganic hybrid resin (for example, silicone/silica) or fluorine-based resin.

Also, provided between the resin adhesive layer 11 and the deep-ultraviolet ray transmitting window member 10 is a metal layer 12 serving as an optical shielding layer having a large reflectivity against deep-ultraviolet rays. The metal layer 12 is constructed by a single layer or multiple layers made of Al, Ni, Ti, Cu, Au, Cr, Mo and Ta. In this case, after the metal layer 12 is formed on the deep-ultraviolet ray transmitting window member 10, the resin adhesive layer 11 is coated on the metal layer 12 and/or the substrate 1-4 of the LTCC substrate 1.

Thus, since the metal layer 12 as the optical shielding layer is provided on the resin adhesive layer 11, deep-ultraviolet rays reflected within the deep-ultraviolet ray transmitting window member 10 can be reflected and/or absorbed by the metal layer 12, so that the resin adhesive layer 11 is not subjected to irradiation of deep-ultraviolet rays. Therefore, the resin adhesive layer 11 would not be chemically-modified to deteriorate, so that the adhesive ability of the resin adhesive layer 11 would not be degraded, thus improving the reliability of the deep-ultraviolet ray emitting package of FIG. 1.

The metal layer 12 of FIGS. 1 and 2 can be replaced by a deep-ultraviolet ray reflective multi-layered dielectric structure 13 which will be explained with reference to FIG. 3.

Figure 3:
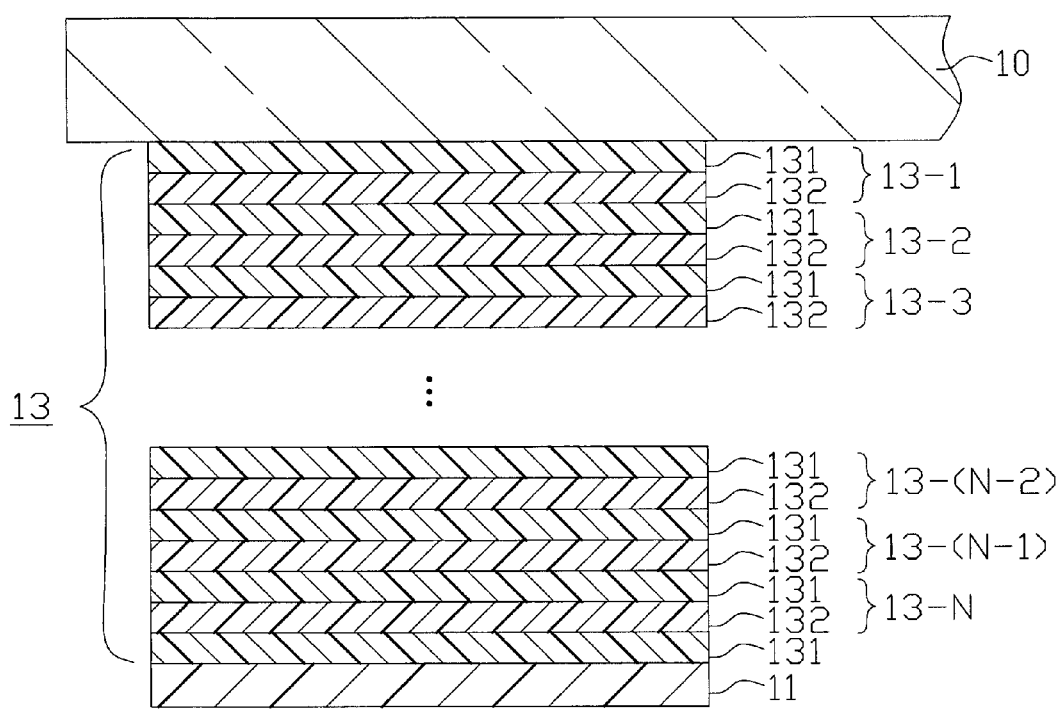
FIG. 3 is a cross-sectional view of a deep-ultraviolet ray reflective multi-layered dielectric structure instead of the metal layer of FIGS. 1 and 2.

In FIG. 3, the deep-ultraviolet ray reflective multi-layered dielectric structure 13 is constructed by laminating pairs 13-1, 13-2, . . . , 13-N, each pair formed by a high refractive-index dielectric layer 131 and a low refractive-index dielectric layer 132 for transmitting deep-ultraviolet rays. Each of the pairs 13-i (i=1, 2, . . . , N) reflects deep-ultraviolet rays with a center wavelength $\lambda_i$ using the light interference phenomenon. In this case, the reflection condition is as follows:

$$n_{131} \cdot d_{131} = n_{132} \cdot d_{132} = \lambda_i / 4$$

where $n_{131}$ is the refractive index of the high refractive index dielectric layer 131;

$d_{131}$ is the thickness of the high refractive index dielectric layer 131;

$n_{132}$ is the refractive index of the low refractive index dielectric layer 132; and $d_{132}$ is the thickness of the low refractive index dielectric layer 132.

In order to reflect deep-ultraviolet rays over a wider wavelength range, the number of the pairs 13-i (i=1, 2, . . . , N) with different center wavelengths $\lambda_i$ needs to be increased. In this case, the larger the difference in refractive index between the high refractive index dielectric layer 131 and the low refractive index dielectric layer 132, the larger the range of wavelengths of reflected deep-ultraviolet rays. Therefore, the materials of the high refractive index dielectric layer 131 and the low refractive index dielectric layer 132 can be selected in view of the range of wavelengths of deep-ultraviolet rays to be reflected.

For example, the high refractive index dielectric layer 131 is made of HfO$_2$ with a refractive index of 2.0 and the low refractive index dielectric layer 132 is made of SiO$_2$ with a refractive index of 1.5. Also, N is assumed to be 15, and an additional HfO$_2$ layer 131 is provided. That is, the refractive index of the deep-ultraviolet ray transmitting window member 10 such as quartz glass on the upper side of the deep-ultraviolet ray reflective multi-layered dielectric structure 13, is low, and also, the resin adhesive layer 11 such as acryl resin on the lower side of the deep-ultraviolet ray reflective multi-layered dielectric structure 13, is low. Therefore, both top and bottom layers of the deep-ultraviolet ray reflective multi-layered dielectric structure 13 are made of HfO$_2$ (high refractive index) adjacent to the low refractive index layers. Thus, the deep-ultraviolet ray reflective multi-layered dielectric structure 13 is formed by sixteen HfO$_2$ layers 131 and fifteen SiO$_2$ layers 132 (2N+1=31). Further, the thickness $d_{131}$ of the HfO$_2$ layers 131 and the thickness $d_{132}$ of the SiO$_2$ layers 132 are gradually changed within the deep-ultraviolet ray reflective multi-layered dielectric structure 13.

The reflectivity of the deep-ultraviolet ray reflective multi-layered dielectric structure 13 for deep-ultraviolet rays can be increased exponentially in dependence upon the layer number (=2N+1). A high reflectivity for deep-ultraviolet rays can be realized over a wavelength range from 260 to 300 nm by the layer number 31 (=2N+1).

Note that the high refractive index dielectric layer 131 can be made of other oxide-based materials such as $ZrO_2$, $Y_2O_3$ and $Sc_2O_3$, instead of $HfO_2$. Also, the low refractive index dielectric layer 132 can be made of $CaF_2$, $MgF_2$ or $BaF_2$, instead of $SiO_2$.

Figure 4:
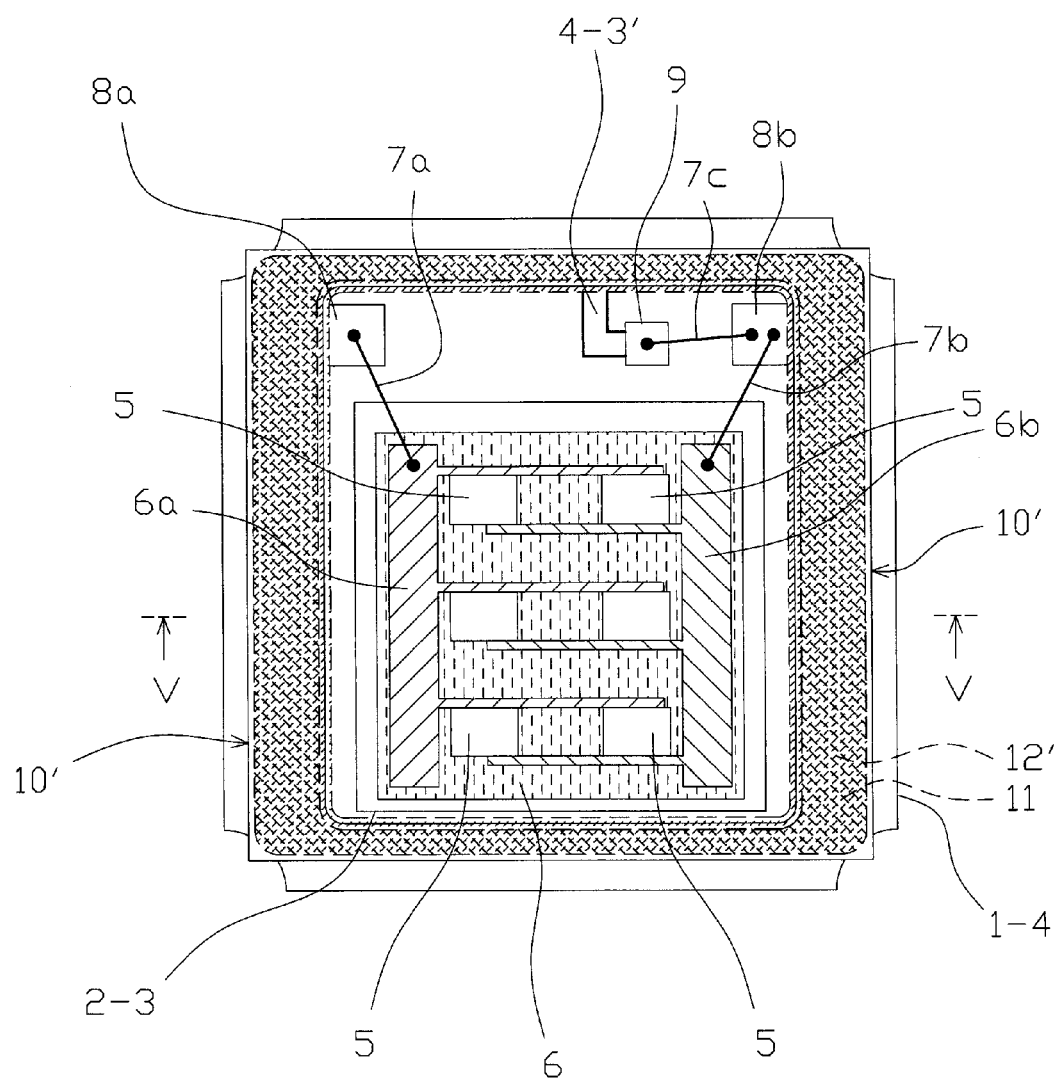
FIG. 4 is a plan diagram illustrating a second embodiment of the deep-ultraviolet ray emitting package according to the presently disclosed subject matter.
Figure 5:
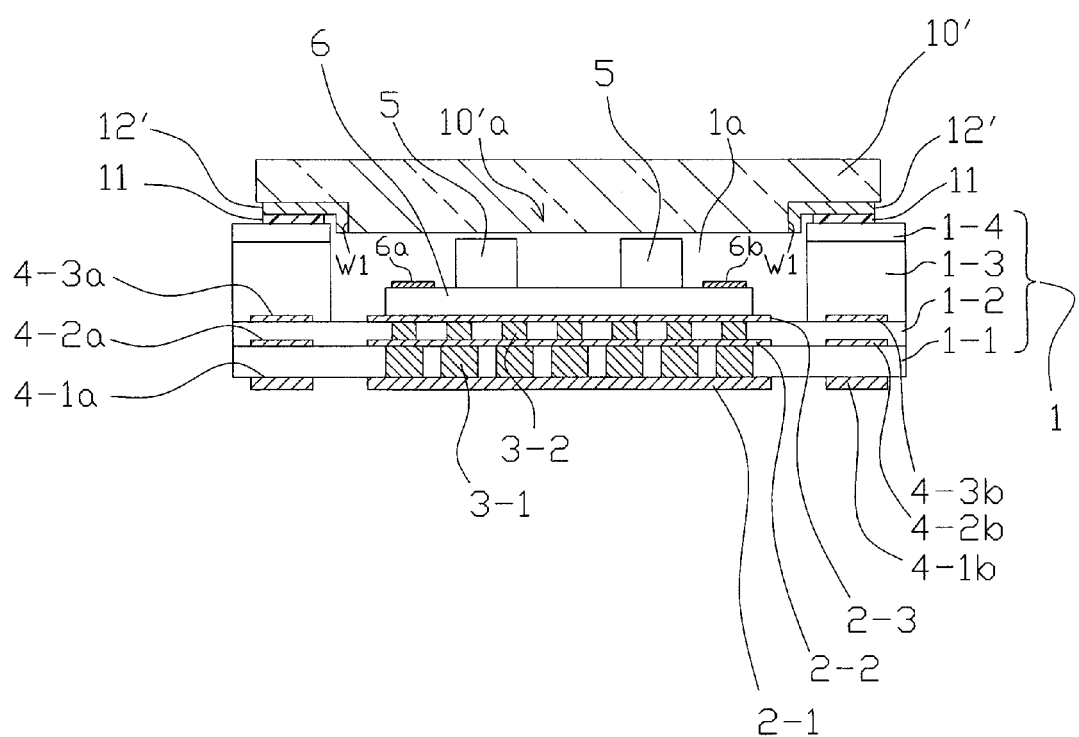
FIG. 5 is a cross-sectional view taken along the line V-V in the deep-ultraviolet ray emitting package of FIG. 4.

FIG. 4 is a plan diagram illustrating a second embodiment of the deep-ultraviolet ray emitting package according to the presently disclosed subject matter, and FIG. 5 is a cross-sectional view taken along the line V-V of FIG. 4.

In FIGS. 4 and 5, a deep-ultraviolet ray transmitting window member 10' having a protrusion 10'a with a perpendicular sidewall W1 on its outer periphery is provided instead of the plate-type deep-ultraviolet ray transmitting window member 10 of FIGS. 1 and 2. The protrusion 10'a of the deep-ultraviolet ray transmitting window member 10' corresponds to the recess 1a of the LTCC substrate 1 and is fitted into the recess 1a of the LTCC substrate 1. In this case, a metal layer 12' corresponding to the metal layer 12 of FIGS. 1 and 2 is provided on an area of the deep-ultraviolet ray transmitting window member 10' corresponding to the substrate 1-4, and is also provided on the perpendicular sidewall W1 of the protrusion 10'a. Further, the metal layer 12' is not always in contact with the substrate 1-4; however, the metal layer 12' covers the sidewall of the resin adhesive layer 11.

Thus, deep-ultraviolet rays reflected within the deep-ultraviolet ray transmitting window member 10' can be further reflected and/or absorbed by the metal layer 12', and also, the direct irradiation of the resin adhesive layer 11 with deep-ultraviolet rays can be suppressed. Further, when the deep-ultraviolet ray transmitting window member 10' is adhered by the resin adhesive layer 11 to the substrate 1-4, traverse sliding of the deep-ultraviolet ray transmitting window member 10' due to the temporary reduction of viscosity of the resin adhesive layer 11 can be suppressed by the perpendicular sidewall W1 of the protrusion 10'a.

FIGS. 6A through 6E are cross-sectional views illustrating modifications of the deep-ultraviolet ray transmitting window member 10' of FIG. 5.

Figure 6:
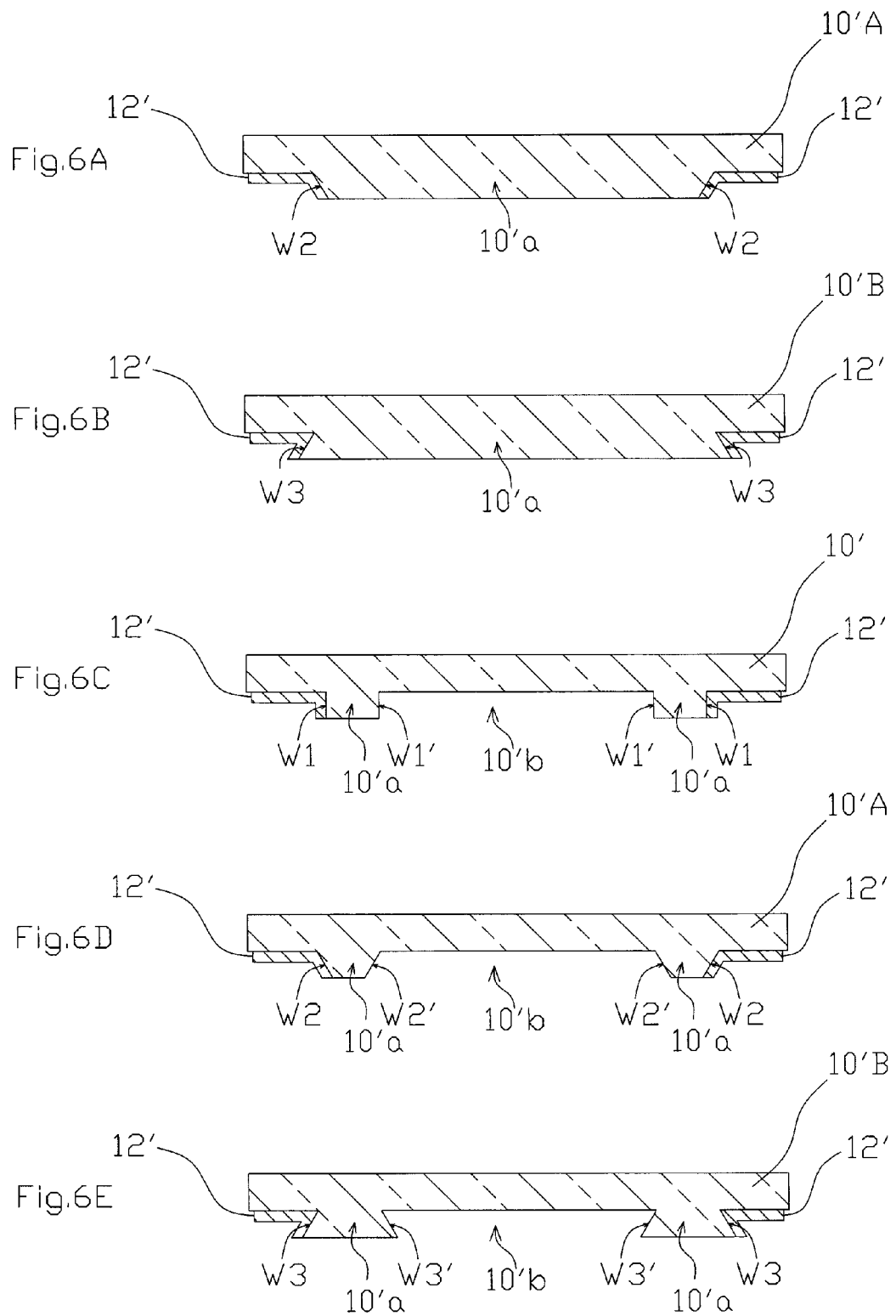
FIGS. 6A through 6E are cross-sectional views illustrating modifications of the deep-ultraviolet ray transmitting window member of FIG. 5.

As illustrated in FIG. 6A, the deep-ultraviolet ray transmitting window member 10' of FIG. 5 is modified to a deep-ultraviolet ray transmitting window member 10'A having a protrusion 10'a with a mesa-shaped sidewall W2. Also, as illustrated in FIG. 6B, the deep-ultraviolet ray transmitting window member 10' of FIG. 5 is modified to a deep-ultraviolet ray transmitting window member 10'B having a protrusion 10'a with a reversely mesa-shaped sidewall W3. As a result, deep-ultraviolet rays reflected within the deep-ultraviolet ray transmitting window member 10'A or 10'B can be further reflected and/or absorbed by the deep-ultraviolet ray metal layer 12'.

As illustrated in FIGS. 6C, 6D and 6E, a recess 10'b can be formed within the protrusion 10'a of FIGS. 5, 6A and 6B. In more detail, in FIG. 6C, the protrusion 10'a has a perpendicular sidewall W1' on its inner periphery in addition to the outer perpendicular sidewall W1 to create the recess 10'b. Also, in FIG. 6D, the protrusion 10'a has a mesa-shaped sidewall W2' in addition to the outer mesa-shaped sidewall W2 to create the recess 10'b. Further, in FIG. 6E, the protrusion 10'a has a reversely mesa-shaped sidewall W3' in addition to the reversely mesa-shaped sidewall W3 to create the recess 10'b. As a result, the extraction efficiency of deep-ultraviolet rays from the deep-ultraviolet ray transmitting window member 10' can be enhanced. Simultaneously, the amount of deep-ultraviolet rays reflected within the deep-ultraviolet ray transmitting window member 10' incident to the metal layer 12' can be reduced.

Figure 7:
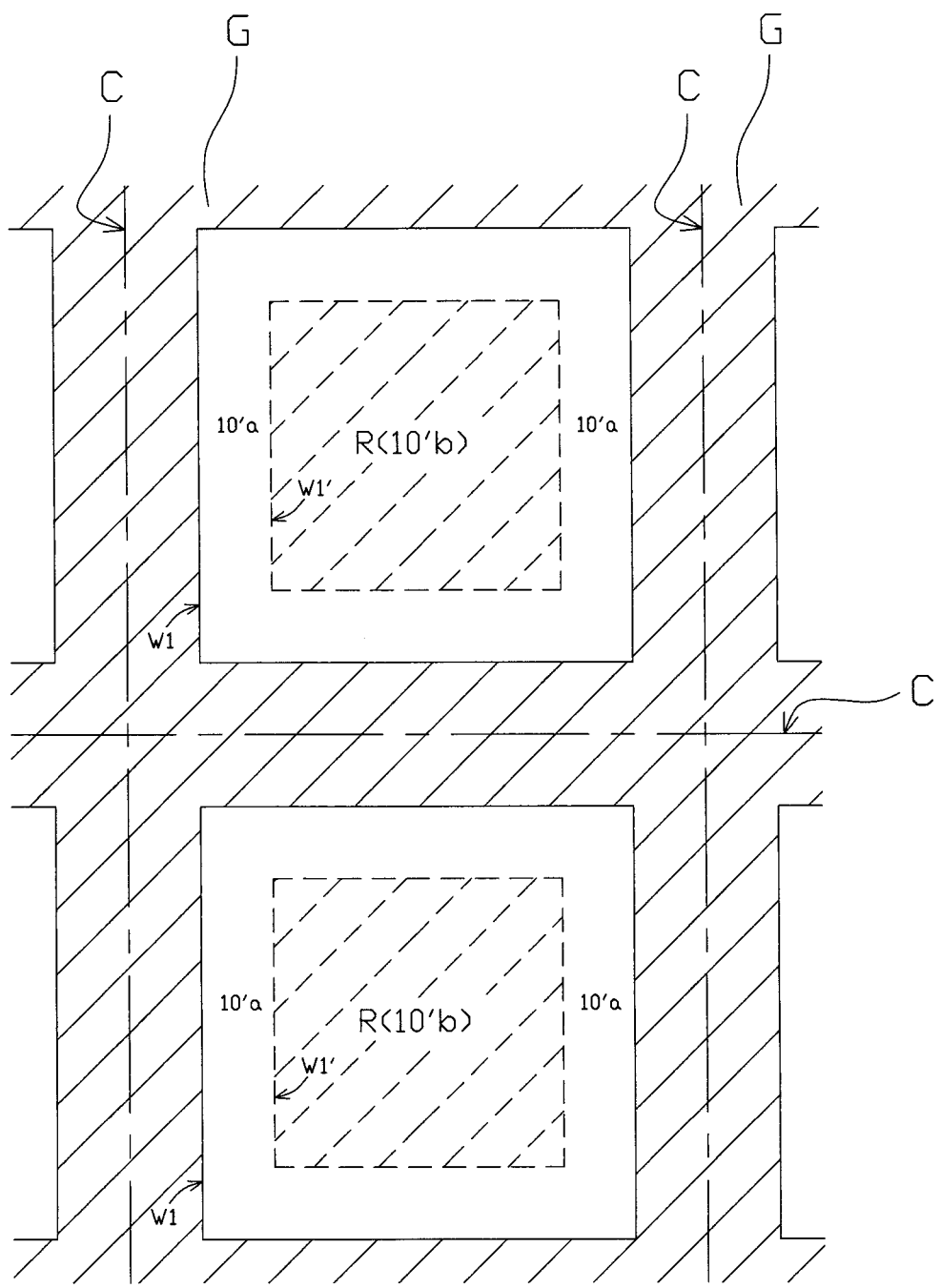
FIG. 7 is a plan view for explaining a method for manufacturing the deep-ultraviolet ray transmitting window members of FIGS. 5 and 6C.

A method for manufacturing the deep-ultraviolet ray transmitting window member 10' of FIGS. 5 and 6C will be explained with reference to FIG. 7.

First, a plate-type member made of quartz glass or the like is prepared. Then, a half cutting operation using dies or the like is performed upon the plate-type member to form a grid of grooves G in the plate-type member. In this case, recesses R for the recess 10'b are also formed in the plate-type member for the deep-ultraviolet ray transmitting window member 10' of FIG. 6C. Finally, a full cutting operation is performed upon the center line portions C of the grooves G of the plate-type member. Thus, the perpendicular sidewall W1 and W1' are formed.

A method for manufacturing the deep-ultraviolet ray transmitting window member 10'A of FIGS. 6A and 6D will be explained next with reference to FIG. 8.

First, a plate-type member made of quartz glass or the like is prepared. Then, a mask is formed on a surface of the plate-type member. Then, a sandblast operation is performed upon the surface of the plate-type member to form a grid of grooves G' in the plate-type member. In this case, recesses R' for the recess 10'b are also formed in the plate-type member for the deep-ultraviolet ray transmitting window member 10A of FIG. 6D. The grooves G' and the recesses R' have tapered walls whose angle such as 70° depends upon the condition of the sandblast operation. Finally, a full cutting operation is performed upon the center line portions C' of the grooves G' of the plate-type member. Thus, the mesa-shaped sidewalls W2 and W2' are formed.

A method for manufacturing the deep-ultraviolet ray transmitting window member 10'B of FIGS. 6B and 6E will be explained below.

Figure 8:
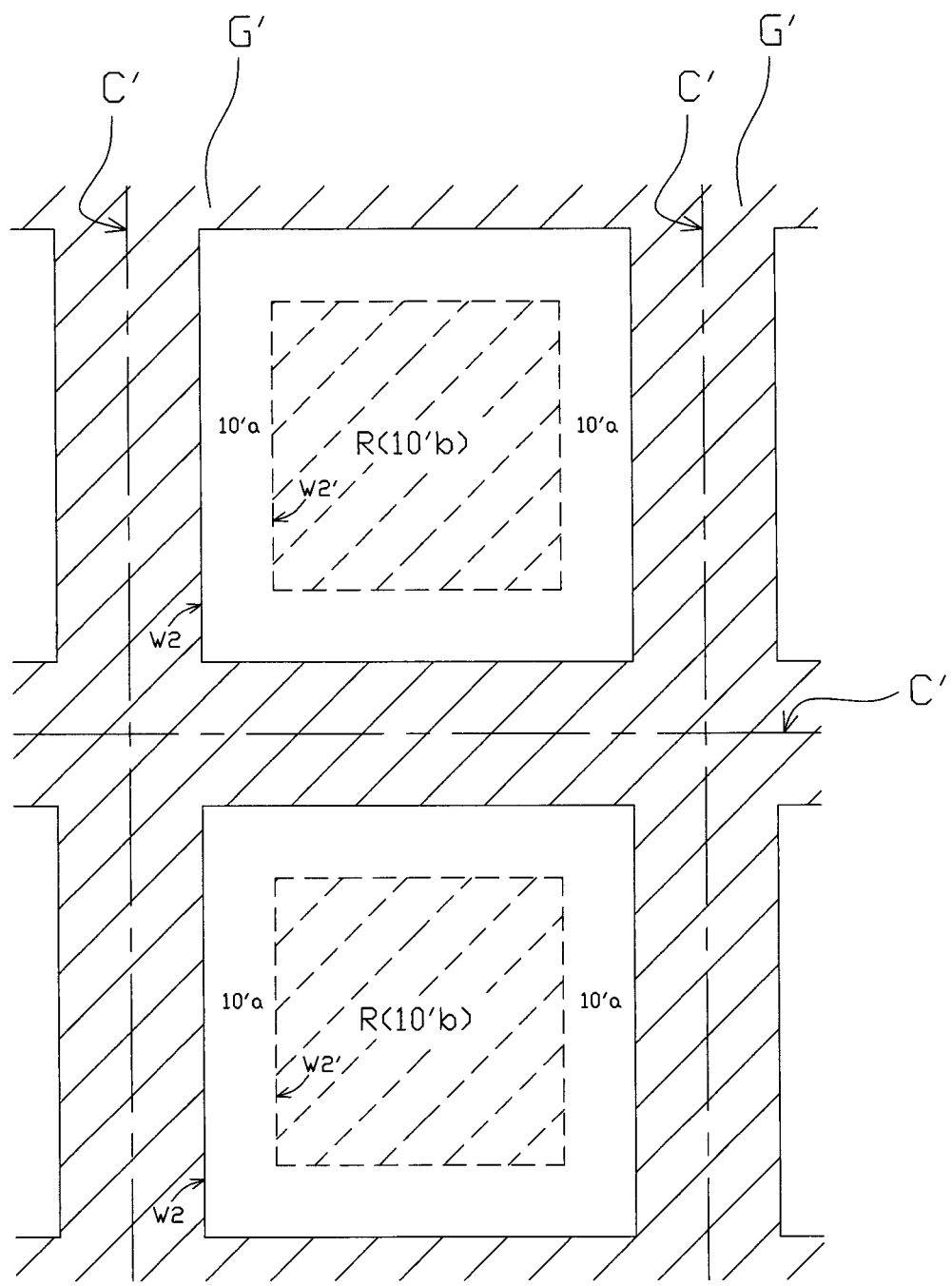
FIG. 8 is a plan view for explaining a method for manufacturing the deep-ultraviolet ray transmitting window members of FIGS. 6A and 6D.

First, a first plate-type member having a grid of grooves G' and recesses R' for the mesa-shaped sidewalls W2 and W2' as illustrated in FIG. 8 is prepared. Then, the first plate-type member is reversed and then, is adhered to a second plate-type member made of quartz glass by an atomic diffusion bonding (ADB) process or a surface-activated bonding (SAB) process. Then, the back plate portion of the first plate-type member is removed by a chemical-mechanical polishing (CMP) process or a chemical etching process using fluoric acid. Finally, a full cutting operation is performed upon the center line portions of the grooves G' of the first plate-type member. Thus, the reversely mesa-shaped sidewalls W3 and W3' are formed.

In FIGS. 4, 5, 6A, 6B, 6C, 6D and 6E, note that the metal layer 12' can be replaced by the deep-ultraviolet reflective multi-layered dielectric structure 13 of FIG. 3.

Figure 9:
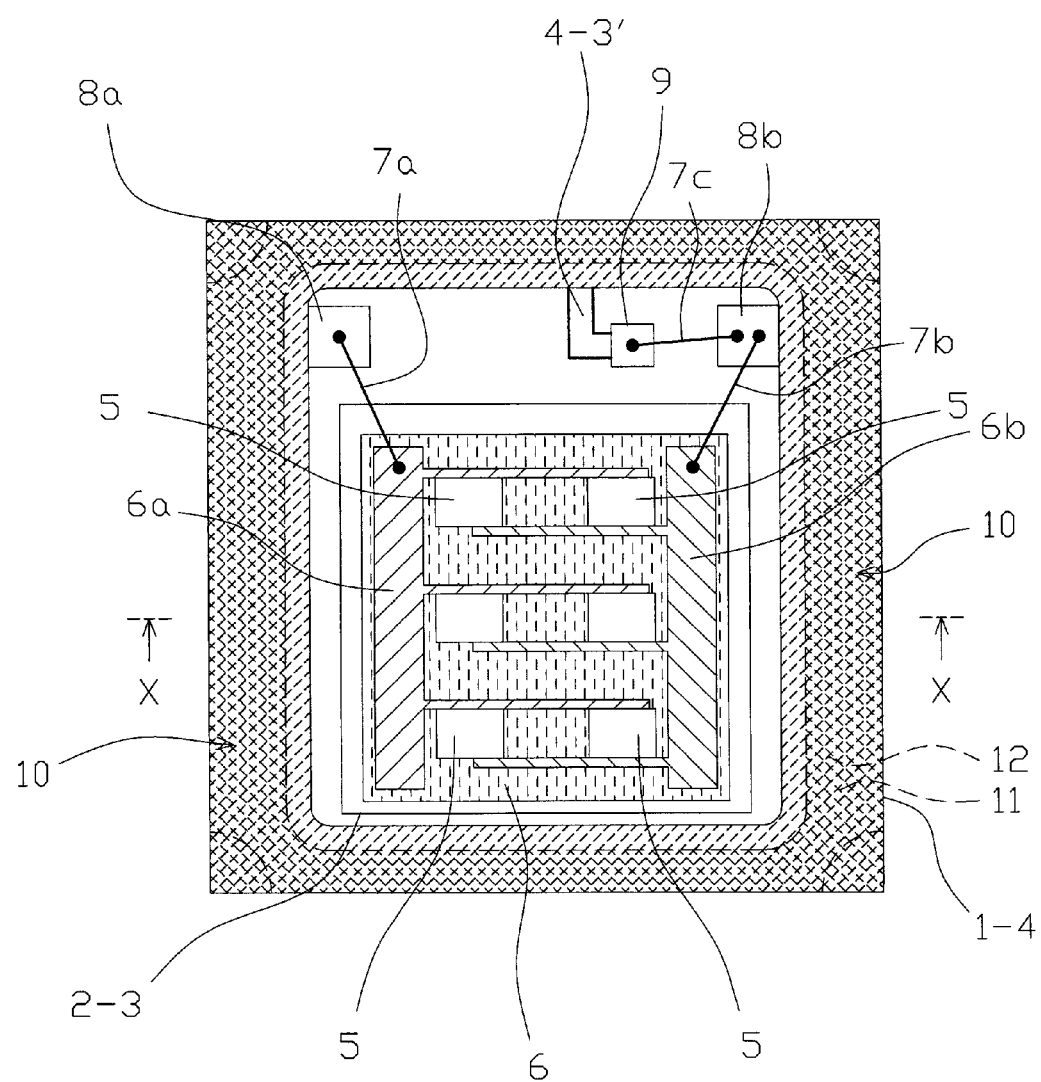
FIG. 9 is a plan diagram illustrating a third embodiment of the deep-ultraviolet ray emitting package according to the presently disclosed subject matter.
Figure 10:
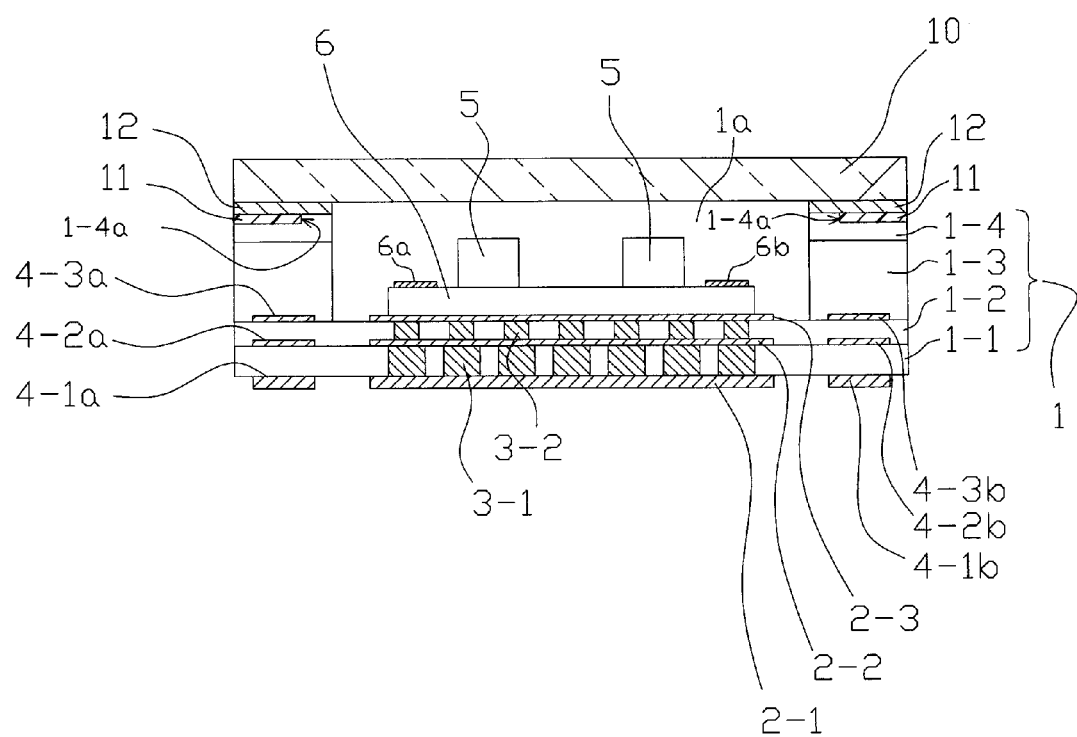
FIG. 10 is a cross-sectional view taken along the line X-X in the deep-ultraviolet ray emitting package of FIG. 9.

FIG. 9 is a plan view illustrating a third embodiment of the deep-ultraviolet ray transmitting package according to the presently disclosed subject matter, and FIG. 10 is a cross-sectional view taken along the line X-X in FIG. 9.

In FIGS. 9 and 10, an outer step 1-4a is provided on an upper face of the substrate 1-4, and the resin adhesive layer 11 is coated on the outer step 1-4a. The resin adhesive layer 11 is thin, for example, about 0.1~0.2 mm so as to reduce its thermal stress. The metal layer 12 is located over the entirety of the substrate 1-4 including the resin adhesive layer 11. In this case, the metal layer 12 is formed on the deep-ultraviolet ray transmitting window member 10 in advance, while the resin adhesive layer 11 is coated on the outer step 1-4a of the substrate 1-4 in advance. Then, the metal layer 12 of the deep-ultraviolet ray transmitting window member 10 is adhered by the resin adhesive layer 11 to the substrate 1-4 of the LTCC substrate 1.

Thus, since the metal layer 12 as the optical shielding layer is provided on the resin adhesive layer 11, deep-ultraviolet rays reflected within the deep-ultraviolet ray transmitting window member 10 can be reflected and/or absorbed by the metal layer 12, so that the resin adhesive layer 11 is not subjected to irradiation of deep-ultraviolet rays. Simultaneously, deep ultraviolet rays directly from the deep-ultraviolet LED elements 5 to the resin adhesive layer 11 can be completely shielded by the substrate 1-4 of the LTCC substrate 1. Therefore, the resin adhesive layer 11 would not be chemically-modified which would cause it to deteriorate, so that the adhesive ability of the resin adhesive layer 11 would not be degraded thus improving the reliability of the deep-ultraviolet ray emitting package of FIG. 9.

Figure 11:
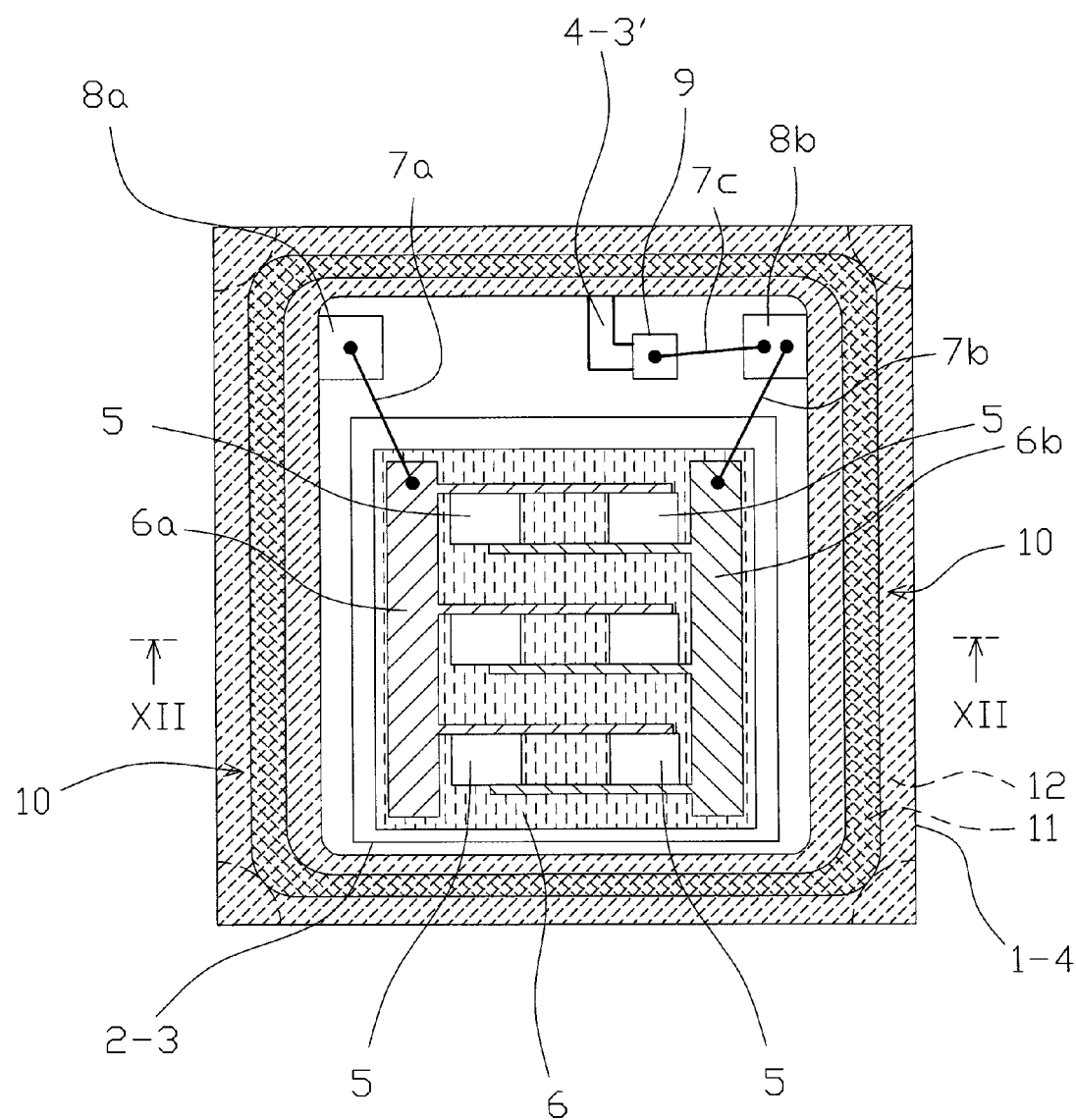
FIG. 11 is a plan diagram illustrating a fourth embodiment of the deep-ultraviolet ray emitting package according to the presently disclosed subject matter.
Figure 12:
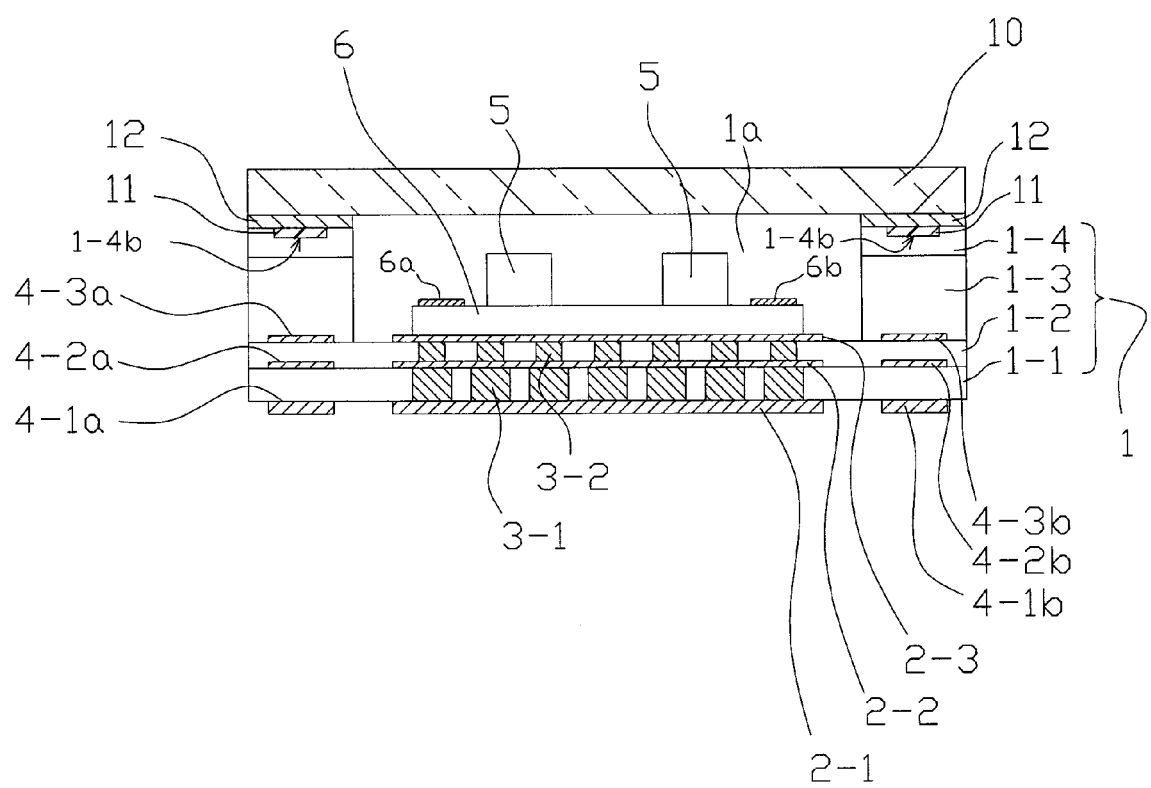
FIG. 12 is a cross-sectional view taken along the line XII-XII in the deep-ultraviolet ray emitting package of FIG. 11.

FIG. 11 is a plan view illustrating a fourth embodiment of the deep-ultraviolet ray transmitting package according to the presently disclosed subject matter, and FIG. 12 is a cross-sectional view taken along the line XII-XII in FIG. 11.

In FIGS. 11 and 12, a recess 1-4b is provided in the substrate 1-4, and the resin adhesive layer 11 is coated in the recess 1-4b. The resin adhesive layer 11 is thin, for example, about 0.1~0.2 mm so as to reduce its thermal stress. The metal layer 12 is located over the entirety of the substrate 1-4 including the resin adhesive layer 11. In this case, the metal layer 12 is formed on the deep-ultraviolet ray transmitting window member 10 in advance, while the resin adhesive layer 11 is coated in the recess 1-4b of the substrate 1-4 in advance. Then, the metal layer 12 of the deep-ultraviolet ray transmitting window member 10 is adhered by the resin adhesive layer 11 to the substrate 1-4 of the LTCC substrate 1. Therefore, the resin adhesive layer 11 would not be chemically-modified which would cause it to deteriorate, so that the adhesive ability of the resin adhesive layer 11 would not be degraded thus improving the reliability of the deep-ultraviolet ray emitting package of FIG. 11.

Figure 13:
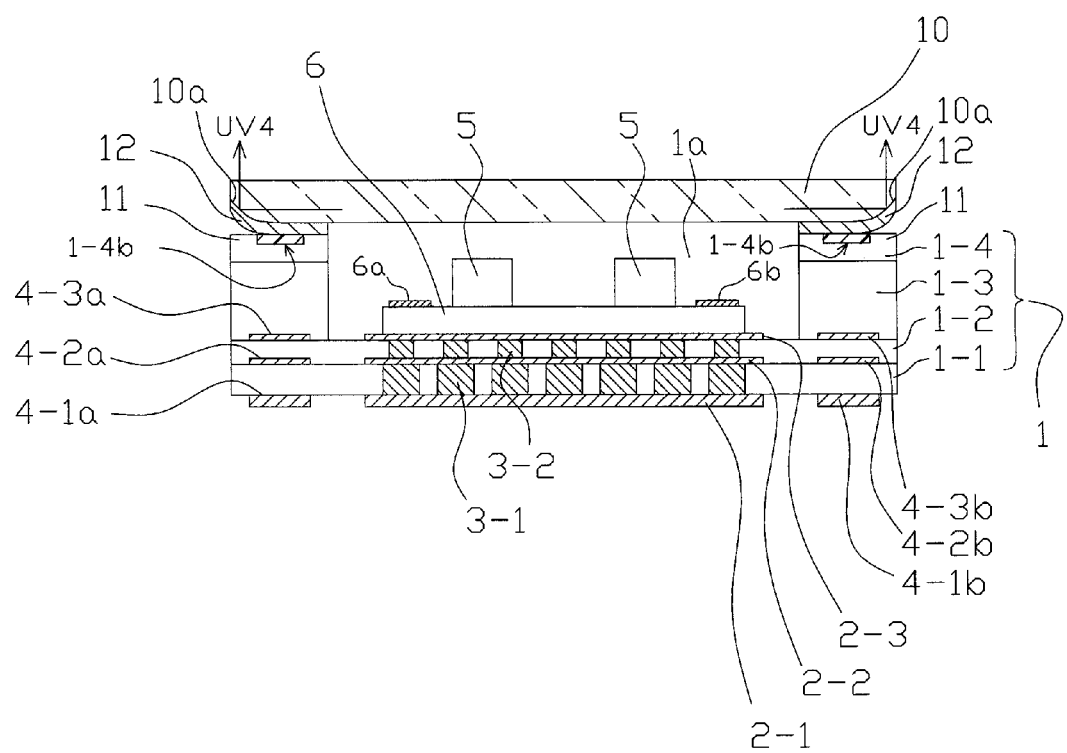
FIG. 13 is a cross-sectional view of a modification of FIG. 12.
Figure 14:
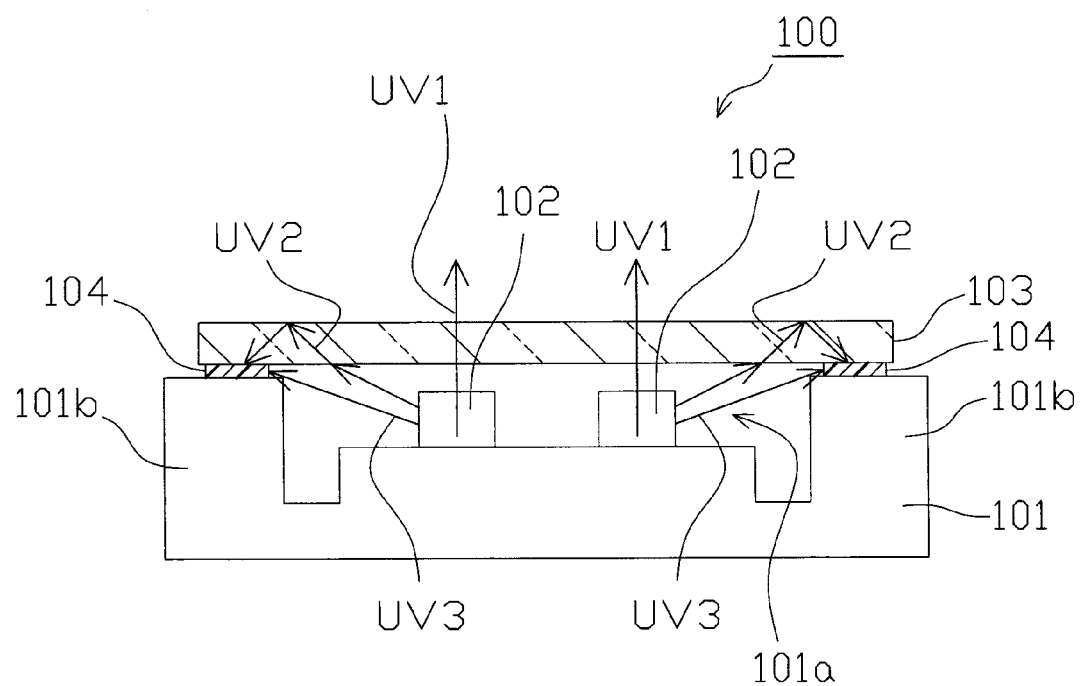
FIG. 14 is a cross-sectional view illustrating a first prior art ultraviolet ray emitting package.
Figure 15:
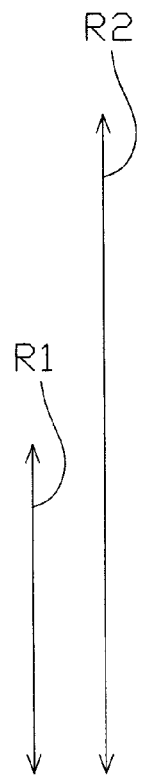
FIG. 15 is a table for showing a relationship among organic groups, bond energy and energy-reduced wavelengths.

FIG. 13 is a cross-sectional view illustrating a modification of the deep-ultraviolet ray emitting package 10 of FIG. 12.

In FIG. 13, a lower outer periphery portion of the deep-ultraviolet ray transmitting window member 10 is chamfered. Therefore, the metal layer 12, which is formed on the deep-ultraviolet ray transmitting window member 10, is bent toward the upper direction at a chamfered portion 10a of the deep-ultraviolet ray transmitting window member 10. Therefore, deep-ultraviolet rays UV4 toward the outer periphery of the deep-ultraviolet ray transmitting member 10 are reflected by the metal layer 12 at the chamfered portion 10a to go in the upward direction. As a result, the deep-ultraviolet ray extraction efficiency can be enhanced. If other deep-ultraviolet ray emitting packages are arranged in the proximity of the deep-ultraviolet ray emitting package of FIG. 13, the leakage of deep-ultraviolet rays from the outer periphery of the deep-ultraviolet emitting package of FIG. 13 toward the other deep-ultraviolet ray emitting packages can be suppressed.

The modification of FIG. 13 can also be applied to the deep-ultraviolet ray emitting packages of FIGS. 1, 4 and 9.

Each of the above-described embodiments relates to a deep-ultraviolet ray emitting package for a short wavelength of about 210 to 310 nm; however, the presently disclosed subject matter can be applied to an ultraviolet ray emitting package for a long wavelength of about 310 nm or more. In this case, the deep-ultraviolet LED elements 5 are replaced by ultraviolet LED elements. Also, the metal layer 12 is replaced by a metal layer whose reflectivity is high over the above-mentioned long wavelength region, or the deep-ultraviolet ray reflective multi-layered dielectric structure 13 is replaced by an ultraviolet ray reflective multi-layered dielectric structure for reflecting ultraviolet rays over the above-mentioned long wavelength range.

Also, in the above-described embodiments, the LTCC substrate 1 can be replaced by a high temperature co-fired ceramics (HTCC) substrate or an AlN substrate. In the HTCC substrate or AlN substrate, the metal via-structures 3-1 and 3-2 are made of W, Mo, Cu or their alloys. Further, in the AlN substrate, since its heat conductivity is large, the metal via-structures 3-1 and 3-2 would be unnecessary.

Figure 16A:
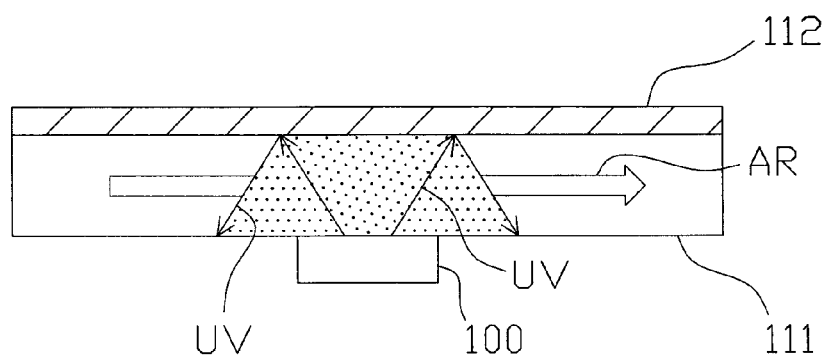
FIGS. 16A, 16B and 16C are views illustrating ultraviolet ray irradiating apparatuses having the ultraviolet ray emitting package of FIG. 14.
Figure 16B:
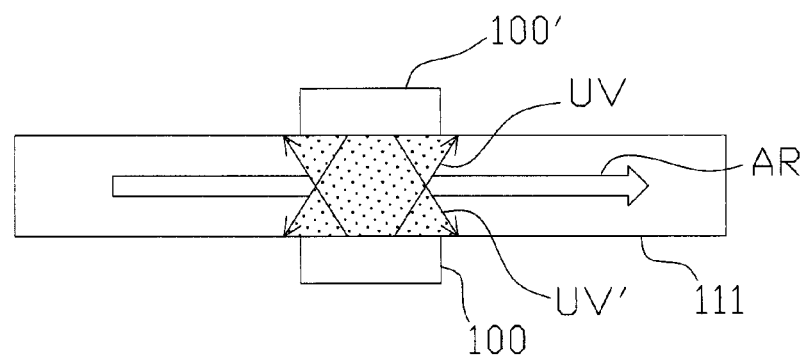
Figure 16C:
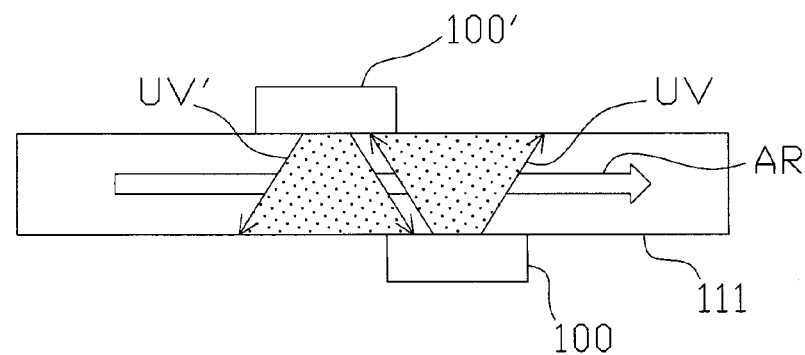
Figure 17:
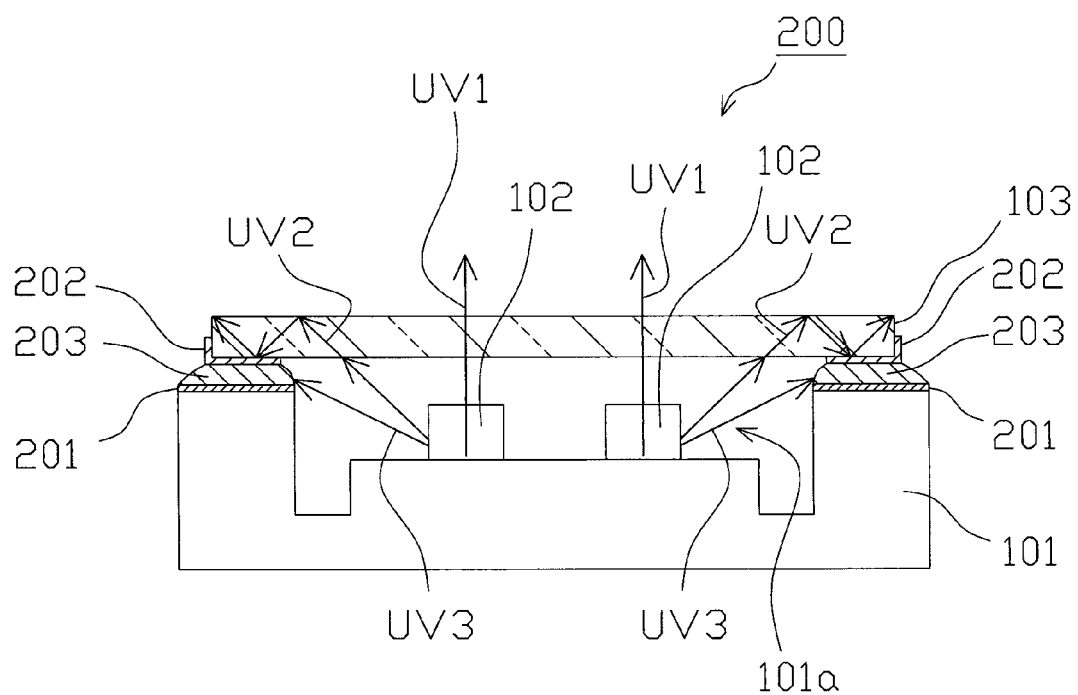
FIG. 17 is a cross-sectional view illustrating a second prior art ultraviolet ray emitting package.

Further, the deep-ultraviolet ray emitting packages (ultraviolet ray emitting packages) of FIGS. 1, 4, 9 and 11 can be applied to deep-ultraviolet ray irradiation apparatuses (ultraviolet ray irradiating apparatuses) as illustrated in FIGS. 16A, 16B and 16C.

Particularly, since the deep-ultraviolet ray emitting packages according to the presently disclosed subject matter can emit deep-ultraviolet rays exhibiting the sterilization effect, the deep-ultraviolet ray emitting packages can be applied to sterilization and purification apparatuses used in water treatment units, water coolers, water servers, medical pure water manufacturing units, moistening units, tableware washers and dental chairs.

It will be apparent to those skilled in the art that various modifications and variations can be made in the presently disclosed subject matter without departing from the spirit or scope of the presently disclosed subject matter. Thus, it is intended that the presently disclosed subject matter covers the modifications and variations of the presently disclosed subject matter provided they come within the scope of the appended claims and their equivalents. All related or prior art references described above and in the Background section of the present specification are hereby incorporated in their entirety by reference.

The invention claimed is:

1. An ultraviolet ray emitting package comprising:
a substrate having an upper portion defining a recess;
an ultraviolet ray emitting element provided within the recess of said substrate;
an ultraviolet ray transmitting window member provided on the upper portion of said substrate to cover the recess of said substrate;
a resin adhesive layer provided between the upper portion of said substrate and said ultraviolet ray transmitting window member; and
an optical shielding layer provided between said resin adhesive layer and said ultraviolet ray transmitting window member.

2. The ultraviolet ray emitting package as set forth in claim 1, wherein said optical shielding layer comprises a metal layer.

3. The ultraviolet ray emitting package as set forth in claim 2, wherein said metal layer comprises at least one of Al, Ni, Ti, Cu, Au, Cr, Mo and Ta.

4. The ultraviolet ray emitting package as set forth in claim 1, wherein said optical shielding layer comprises an ultraviolet ray reflective multi-layered dielectric structure.

5. The ultraviolet ray emitting package as set forth in claim 4, wherein said ultraviolet ray emitting element comprises a deep-ultraviolet ray emitting element, and said ultraviolet ray transmitting window member comprises a deep-ultraviolet ray transmitting window member, said ultraviolet ray reflection multi-layered dielectric structure comprising a deep-ultraviolet ray reflective multi-layered dielectric structure.

6. The ultraviolet ray emitting package as set forth in claim 1, wherein said ultraviolet ray transmitting window member comprises a protrusion fitted into the recess of said substrate.

7. The ultraviolet ray emitting package as set forth in claim 6, wherein said prostrations has an outer sidewall that is perpendicular, mesa-shaped or reversely mesa-shaped.

8. The ultraviolet ray emitting package as set forth in claim 6, wherein said optical shielding layer is provided on an outer sidewall of the protrusion of said ultraviolet ray transmitting package.

9. The ultraviolet ray emitting package as set forth in claim 6, wherein a recess is provided in the protrusion of said ultraviolet ray transmitting window member.

10. The ultraviolet ray emitting package as set forth in claim 9, wherein said protrusion has an inner sidewall that is perpendicular, mesa-shaped or reversely mesa-shaped.

11. The ultraviolet ray emitting package as set forth in claim 1, wherein an outer step is provided in the upper portion of said substrate, said resin adhesive layer being provided in said outer step.

12. The ultraviolet ray emitting package as set forth in claim 1, wherein a recess is provided in the upper portion of said substrate, said resin adhesive layer being provided in said recess.

13. The ultraviolet ray emitting package as set forth in claim 1, wherein a chamfered portion is provided on a lower outer periphery of said ultraviolet ray transmitting window member, said optical shielding layer being provided on said chamfered portion.

14. The ultraviolet ray emitting package as set forth in claim 1, wherein said ultraviolet ray emitting element comprises a deep-ultraviolet ray emitting element, and said ultraviolet ray transmitting window member comprises a deep-ultraviolet ray transmitting window member.

15. An ultraviolet irradiating apparatus comprising:

an ultraviolet ray transmitting casing for flowing gas or water to be processed there through: and said ultraviolet ray emitting package as set forth in claim 1 provided on an outer face of said ultraviolet ray transmitting casing.

16. The ultraviolet irradiating apparatus as set forth in claim 15, wherein said ultraviolet ray emitting package comprises a deep-ultraviolet ray emitting package.

\* \* \* \* \*